(12) United States Patent
Dorman et al.

(10) Patent No.: US 9,417,208 B2
(45) Date of Patent: Aug. 16, 2016

(54) DUAL FET SENSOR FOR SENSING BIOMOLECULES AND CHARGED IONS IN AN ELECTROLYTE

(75) Inventors: Donald Dorman, Carmel, NY (US); Tak Ning, Yorktown Heights, NY (US); Sufi Zafar, Briarcliff Manor, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 1026 days.

(21) Appl. No.: 13/571,389

(22) Filed: Aug. 10, 2012

(65) Prior Publication Data

US 2012/0298531 A1  Nov. 29, 2012

Related U.S. Application Data

(62) Division of application No. 12/756,628, filed on Apr. 8, 2010.

(51) Int. Cl.
  *G01N 27/414* (2006.01)
  *G01N 27/333* (2006.01)
  *G01N 27/327* (2006.01)

(52) U.S. Cl.
  CPC ........ *G01N 27/4145* (2013.01); *G01N 27/3271* (2013.01); *G01N 27/3335* (2013.01); *G01N 27/414* (2013.01)

(58) Field of Classification Search
  CPC .... B82Y 15/00; H01L 27/1203; H01L 21/84; B01L 3/502753; G01N 27/4145; G01N 27/414; G01N 27/3271; G01N 27/3335
  See application file for complete search history.

(56) References Cited

U.S. PATENT DOCUMENTS

| | | |
|---|---|---|
| 3,562,553 A | 2/1971 | Roth |
| 3,766,371 A | 10/1973 | Suzuki |
| 4,173,818 A | 11/1979 | Bassous et al. |
| 4,238,757 A | 12/1980 | Schenck |

(Continued)

FOREIGN PATENT DOCUMENTS

| | | |
|---|---|---|
| DE | 10254158 A1 | 6/2004 |
| JP | 2007533987 T | 11/2007 |
| WO | 2008068719 A1 | 6/2008 |

OTHER PUBLICATIONS

Deen et al. (CN 2 619 000 A1).*

(Continued)

*Primary Examiner* — Luan Van
*Assistant Examiner* — Steven Rosenwald
(74) *Attorney, Agent, or Firm* — Cantor Colburn LLP; Vazken Alexanian

(57) ABSTRACT

A method for operating a sensor for biomolecules or charged ions, the sensor comprising a first field effect transistor (FET) and a second FET, wherein the first FET and the second FET comprise a shared node includes placing an electrolyte containing the biomolecules or charged ions on a sensing surface of the sensor, the electrolyte comprising a gate of the second FET; applying an inversion voltage to a gate of the first FET; making a first electrical connection to an unshared node of the first FET; making a second electrical connection to unshared node of the second FET; determining a change in a drain current flowing between the unshared node of the first FET and the unshared node of the second FET; and determining an amount of biomolecules or charged ions contained in the electrolyte based on the determined change in the drain current.

6 Claims, 4 Drawing Sheets

(56) References Cited

U.S. PATENT DOCUMENTS

| | | | |
|---|---|---|---|
| 4,657,658 | A | 4/1987 | Sibald |
| 4,984,045 | A | 1/1991 | Matsunaga |
| 5,160,597 | A | 11/1992 | Colapicchioni et al. |
| 5,309,085 | A | 5/1994 | Sohn |
| 6,258,606 | B1 | 7/2001 | Kovacs |
| 6,525,354 | B2 | 2/2003 | Masleid |
| 6,682,936 | B2 | 1/2004 | Kovacs |
| 6,911,383 | B2 | 6/2005 | Doris et al. |
| 6,956,258 | B2 * | 10/2005 | Peng .............................. 257/298 |
| 7,019,305 | B2 | 3/2006 | Eversmann et al. |
| 7,116,113 | B1 | 10/2006 | Thompsen et al. |
| 7,150,997 | B2 | 12/2006 | Kovacs |
| 7,151,301 | B2 | 12/2006 | Yoo et al. |
| 7,291,496 | B2 | 11/2007 | Holm-Kennedy |
| 7,317,216 | B2 | 1/2008 | Holm-Kennedy |
| 7,357,018 | B2 | 4/2008 | Curry et al. |
| 7,394,263 | B2 | 7/2008 | Pechstein et al. |
| 7,507,675 | B2 | 3/2009 | Zuilhof et al. |
| 2004/0109075 | A1 | 6/2004 | Tsunai |
| 2004/0256655 | A1 | 12/2004 | Kan et al. |
| 2005/0040483 | A1 | 2/2005 | Offenhauser et al. |
| 2005/0053524 | A1 | 3/2005 | Keersmaecker et al. |
| 2005/0068015 | A1 | 3/2005 | Hazucha et al. |
| 2005/0230271 | A1 * | 10/2005 | Levon et al. .................. 205/789 |
| 2006/0145194 | A1 | 7/2006 | Barron et al. |
| 2006/0181925 | A1 | 8/2006 | Specht et al. |
| 2006/0246443 | A1 | 11/2006 | Bockelmann et al. |
| 2006/0272942 | A1 | 12/2006 | Sirringhaus |
| 2007/0069285 | A1 | 3/2007 | Takami |
| 2007/0080440 | A1 | 4/2007 | Cheng et al. |
| 2007/0159216 | A1 | 7/2007 | Lee et al. |
| 2007/0252176 | A1 | 11/2007 | Shim et al. |
| 2008/0035494 | A1 | 2/2008 | Gomez et al. |
| 2008/0151088 | A1 | 6/2008 | Frey et al. |
| 2008/0303095 | A1 | 12/2008 | Xiong et al. |
| 2008/0315861 | A1 | 12/2008 | Chung et al. |
| 2009/0072313 | A1 | 3/2009 | Cai et al. |
| 2009/0127589 | A1 | 5/2009 | Rothberg et al. |
| 2010/0164102 | A1 | 7/2010 | Rachmady et al. |
| 2010/0248284 | A1 | 9/2010 | Chen et al. |
| 2011/0033952 | A1 | 2/2011 | Khater et al. |

OTHER PUBLICATIONS

Examination Report under Section 18(e) for Application GB1207849.9; Date of Report: Aug. 21, 2013; 7 pgs., cited on the IDS dated Oct. 8, 2013.*
Examination Report under Section 18(e) for Application GB1207849.9; Date of Report: Aug. 21, 2013; 7 pgs.
Khater, et al., U.S. Appl. No. 12/537,063, entitled "Sensor for Biomolecules ", filed Aug. 6, 2009.
Non-Final Office Action dated Jan. 10, 2012 for U.S. Appl. No. 12/537,063, filed Aug. 6, 2009; Khater et al.; 32 pages.
F. Patolsky et al., Electrical detection of single viruses, PNAS, Sep. 28, 2004, pp. 14017-14022, vol. 101, No. 39, PNAS.
Final Office Action dated Jul. 25, 2012, for U.S. Appl. No. 12/537,063.
H. Im et al., A dielectric-modulated field-effect transistor for biosensing, Nature Nanotechnology, Jul. 2007, pp. 430-434, vol. 2, Nature Publishing Group.
Han, Label-free detection of biomlecules by a field-effect transistor microarray biosensor with bio-functionalized gate surfaces, Dec. 2006 [retrieved on Mar. 17, 2011]. Retrieved from the internet:,URL: http://juwel.fz-juelich.de:8080/dspace/bitstream/2128/2597/1/Juel_4227_Han.pdf.
Hinkle, C.L., et al.; "Enhanced Tunneling in Stacked Gate Dielectrics with Ultra-Thin HFO2 (ZRO2) Layers Sandwiched Between Thicker SIO2 Layers"; Surface Science 566-268; p. 1185-1189; 2004.
Huang, et al. "Development of Active Matrix Biosensor Array for Cell Screening". Proc. of IEEE Sensors 2004.
Notification of Transmittal of the International Search Report and the Written Opinion of the International Searching Authority, or the Declaration; PCT/US11/20007;Apr. 6, 2011.
U.S. Appl. No. 12/651,504. Non Final Office Action Mailed Mar. 4, 2011.
Final Office Action dated Apr. 26, 2012 for U.S. Appl. No. 13/232,395.
Non-final Office Action dated Jan. 6, 2012 for U.S. Appl. No. 13/232,395.
International Search Report and Written Opinion ; International Application No. PCT/EP2011/052981; International Filing Date: Mar. 1, 2011; Date of Mailing: Jun. 30, 2011; 10 pages.
K. Nakazato, et al. "CMOS Cascode Source-Drain Follower for Monolithically Integrated Biosensor Array". IEICE Trans. Electron., vol. E91-C, No. 9 Sep. 2008. pp. 1505-1515.
Leobandung, E., et al.; "Wire-Channel and Wrap-Around-Gate-Metal-Oxide-Semiconductor Field-Effect Transistors With a Significant Reduction of Short Channel Effects"; J. Vac. Sci. Technol. B.; vol. 15, No. 6; p. 2791-2794; Nov./Dec. 1997.
Lee, et al., Ion-Sensitive Field-Effect Transistor for Biological Sensing, Sensors 2003, 9, 7111-7131; doi:10.3390/s90907111 [online], Sep. 7, 2009 [retrieved on Mar. 17, 2011]. Retrieved from the Internet:,URL:http://www.mdpi.com/1424-8220/9/7111/pdf.
Maher, Electrical Engineering 234 Electrical Engineering Circuit Laboratory, Manual [online], Jun. 1992 [retrieved on Mar. 17, 2011]. Retrieved from the Internet:,URL:http://www.coe.montana.edu/ee/rmaher/teaching/EEngr_234_Labs_maher.pdf>p. 8-1 to 8-20.
Papadopoulos, S., et al.; "Protein Diffusion in Living Skeletal Muscle Fibers: Dependence on Protein Size, Fiber Type, and Contraction"; Biophysical Journal; vol. 79; p. 2084-2094; Oct. 2000.
R. Thewes, et al. "CMOS-based Biosensor Arrays". Proceedings of the Design, Automation and Test in Europe Conference and Exhibition (Date'05), 2 pages.
Simpson, Robert E.; "Introductory Electronics for Scientists and Engineers"; Second Edition; Chapter 6, Allyn and Bacon; p. 258-284; 1987.
Stern, et al; "Label-Free Immunodetection With CMOS-Compatible Seminconducting Nanowires"; Nature; vol. 445; p. 519-522; Feb. 2007.
Wu, et al.; "Single-Crystal Metallic Nanowires and Metal/Semiconductor Nanowire Heterostructures"; Letters to Nature; vol. 430; p. 61-65; Jul. 2004.

* cited by examiner

US 9,417,208 B2

DUAL FET SENSOR FOR SENSING BIOMOLECULES AND CHARGED IONS IN AN ELECTROLYTE

CROSS-REFERENCE TO RELATED APPLICATION

This application is a divisional of U.S. application Ser. No. 12/756,628, filed on Apr. 8, 2010 the disclosure of which are incorporated herein by reference in their entirety.

FIELD OF INVENTION

This disclosure relates generally to the field of sensing of biomolecules and charged ions in an electrolyte solution.

DESCRIPTION OF RELATED ART

A field effect transistor (FET), comprising a source, a drain, and a gate, may be used as a sensor for various types of biomolecules, including but not limited to charged ions, such as H+ or Ca++, proteins, glucose, or viruses, by using an electrolyte containing the biomolecules as the FET gate (see P. Bergveld, Sensors and Actuators B 88 (2003) 1-20, for further information). In operation, a voltage may be applied to the FET gate electrolyte by immersing an electrode into the electrolyte, and connecting the electrode to a voltage source. The presence of the electrode may cause the sensor to have a relatively cumbersome setup, and may limit miniaturization and automation of the sensor. The electrode, which may comprise a silver wire coated with a silver chloride layer, may also cause reliability issues in the sensor over time, due to chemical changes in the electrode material that may occur with prolonged use.

A FET based-sensor that does not require an electrode immersed in the electrolyte may comprise a back-gated silicon nanowire FET structure (See E. Stern et al, Nature, Vol. 445, page 519 (2007) for further information). A back gated FET uses a layer of buried oxide as the gate dielectric. The buried oxide may be relatively thick, resulting in a relatively large sub-threshold slope (greater than 300 mV/decade) and high threshold voltages, and as result, the sensitivity of the sensor may be degraded and the sensing voltage is high. In order to improve sensitivity, the silicon nanowire diameters may be made increasingly thin; however, a relatively thin silicon nanowire may lead to yield issues in sensor fabrication. In order to lower the sensing voltage, the thickness of the buried oxide may be made thinner and the fixed charge density in the buried oxide layer may be reduced. The fabrication processes for thin silicon nanowires and thin buried oxide layer with reduced fixed charge density may be relatively complex and costly compared to fabrication process for regular FETs.

SUMMARY

In one aspect, a method for operating a sensor for biomolecules or charged ions, the sensor comprising a first field effect transistor (FET) and a second FET, wherein the first FET and the second FET comprise a shared node includes placing an electrolyte containing the biomolecules or charged ions on a sensing surface of the sensor, the electrolyte comprising a gate of the second FET; applying an inversion voltage to a gate of the first FET; making a first electrical connection to an unshared node of the first FET; making a second electrical connection to unshared node of the second FET; determining a change in a drain current flowing between the unshared node of the first FET and the unshared node of the second FET; and determining an amount of biomolecules or charged ions contained in the electrolyte based on the determined change in the drain current.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of systems and methods for a dual FET sensor for biomolecules and charged ions are provided, with exemplary embodiments being discussed below in detail. A FET-based sensor structure may comprise two serially connected n-type or p-type metal oxide field effect transistors (MOSFETs, or FETs), where the first FET is a control FET and the second FET is a sense FET having an electrolyte as the gate. The control FET and the sense FET may share a node. The gate dielectric surface of the sense FET may be functionalized such that the surface of the gate dielectric specifically binds the type of biomolecules that the dual FET sensor is used to detect. The biomolecules in the electrolyte bind to the functionalized gate dielectric surface of the sense FET, causing a change in a drain current of the sensor. An amount of biomolecules that are present in the electrolyte may be determined based on the change in the drain current. Use of a dual FET sensor eliminates the need to immerse an electrode in the electrolyte.

Figure 1:
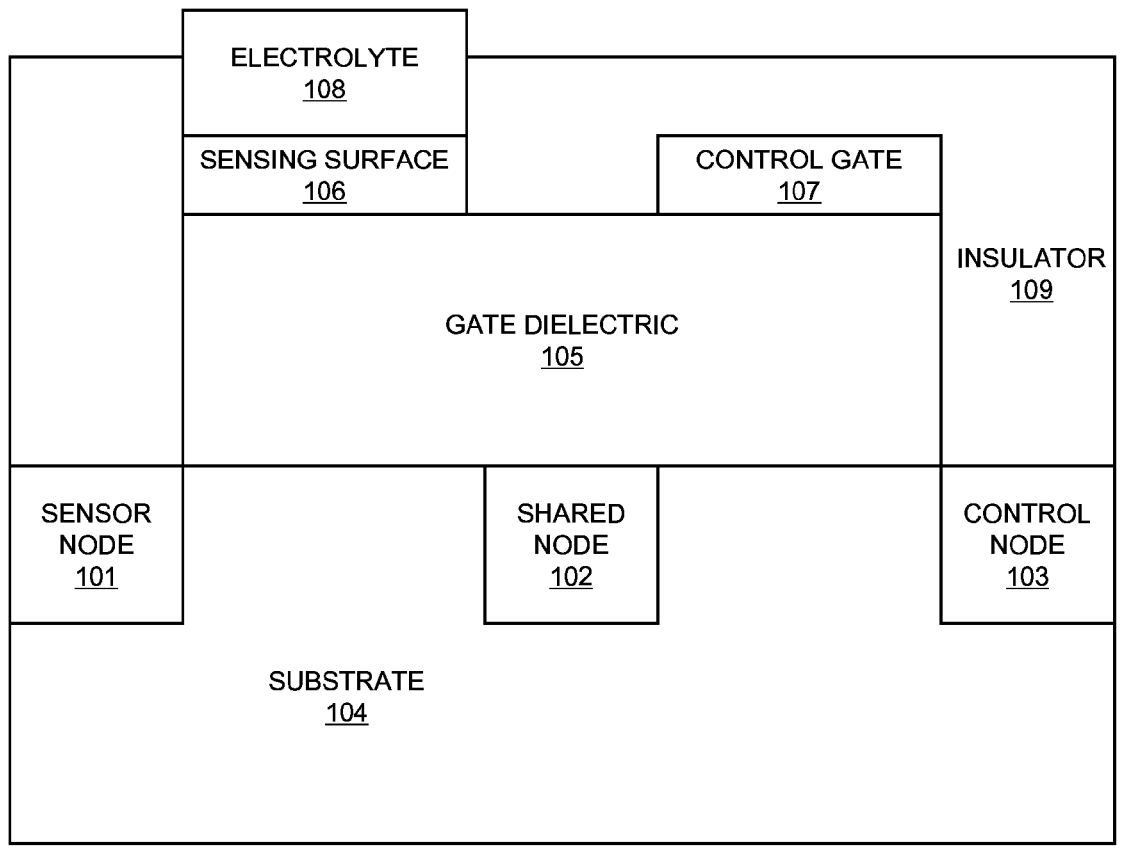
FIG. 1 illustrates an embodiment of a dual FET sensor.

FIG. 1 illustrates an embodiment of a dual FET sensor 100, comprising a control FET and a sense FET. The sense FET comprises shared node 102 and sensor node 101, which act as the sense FET source/drain, and a gate comprising the electrolyte 108. The surface of gate dielectric 105 that is in contact with the electrolyte 108 is functionalized to form sensing surface 106. The control FET comprises shared node 102 and control node 103, which act as the control FET source/drain, and control gate 107. The dual FET sensor 100 is built on a substrate 104; sensor node 101, shared node 102, and control node 103 are formed in substrate 104. An insulating material 109 may be located over the substrate 104. Gate dielectric 105 is located over substrate 104, sensor node 101, shared node 102, and control node 103. In operation, electrical connections are made to sensor node 101, control node 103, and control gate 107, which may comprise metal lines (not shown), and a drain current ($I_d$) flows through dual FET sensor 100 between sensor node 101 and control node 103.

Figure 2:
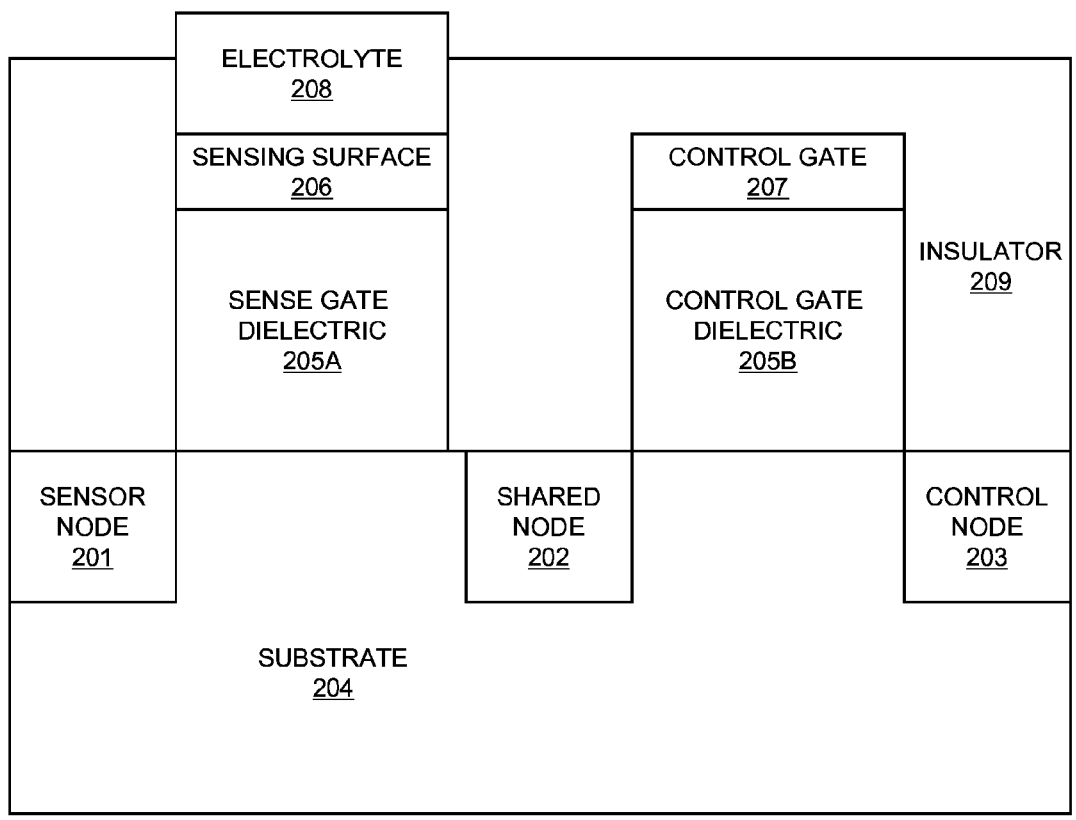
FIG. 2 illustrates an embodiment of a dual FET sensor.

FIG. 2 illustrates an alternate embodiment of a dual FET sensor 200. Dual FET sensor 200 also comprising a control FET and a sense FET. The sense FET comprises shared node 202 and sensor node 201, which act as the sense FET source/drain, and a gate comprising the electrolyte 208 on sense gate dielectric 205A. The surface of gate dielectric 205A that is in contact with the electrolyte 208 is functionalized to form sensing surface 206. The control FET comprises shared node 202 and control node 203, which act as the control FET source/drain, and control gate 207 on control gate dielectric 205B. The dual FET sensor 200 is built on a substrate 104; sensor node 201, shared node 202, and control node 203 are formed in substrate 204. An insulating material 209 may be located over the substrate 204. In operation, electrical connections, which may comprise metal lines (not shown), are made to sensor node 201, control node 203, and control gate 207, and a drain current ($I_d$) flows through dual FET sensor 200 between sensor node 201 and control node 203.

Figure 3:
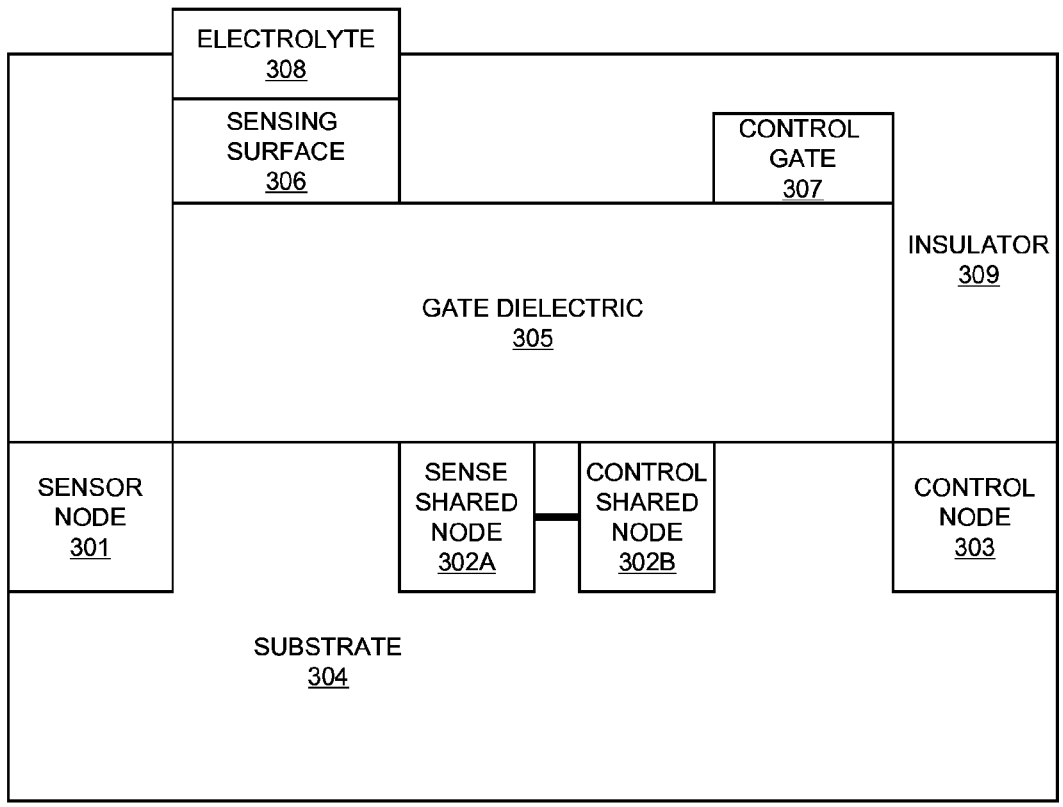
FIG. 3 illustrates an embodiment of a dual FET sensor.

FIG. 3 illustrates an alternate embodiment of a dual FET sensor 200. Dual FET sensor 300 also comprising a control FET and a sense FET. The sense FET comprises sense shared node 302A and sensor node 301, which act as the sense FET source/drain, and a gate comprising the electrolyte 308 on gate dielectric 305. The surface of gate dielectric 305 that is in contact with the electrolyte 308 is functionalized to form sensing surface 306. The control FET comprises control shared node 302B and control node 303, which act as the control FET source/drain, and control gate 307 on gate dielectric 205. Sense shared node 302A is connected to control shared node 302B. The dual FET sensor 300 is built on a substrate 304; sensor node 301, shared nodes 302A-B, and control node 303 are formed in substrate 304. An insulating material 309 may be located over the substrate 304. In operation, electrical connections, which may comprise metal lines (not shown), are made to sensor node 301, control node 303, and control gate 307, and a drain current ($I_d$) flows through dual FET sensor 300 between sensor node 301 and control node 303.

The control gate (107, 207, and 307) may comprise polysilicon or a metal in some embodiments. The sensor node (101, 201, 301), shared node (102, 202, 302A-B), and control node (103, 203, 303), each have the same doping type (n+-type or p+-type) in some embodiments. Substrate 104, 204, and 304 may comprise bulk silicon or silicon-on-insulator, and may have a doping type (n-type or p-type) that is opposite the doping type of the nodes (101-103, 201-203, 301-303) in some embodiments. The gate dielectric (105, 205A-B, 305) may comprise $SiO_2$, SiON, a high-k material, or a bilayer of SiO2 and high k with an equivalent oxide thickness (EOT) greater than 20 angstroms (A) in some embodiments.

Figure 4:
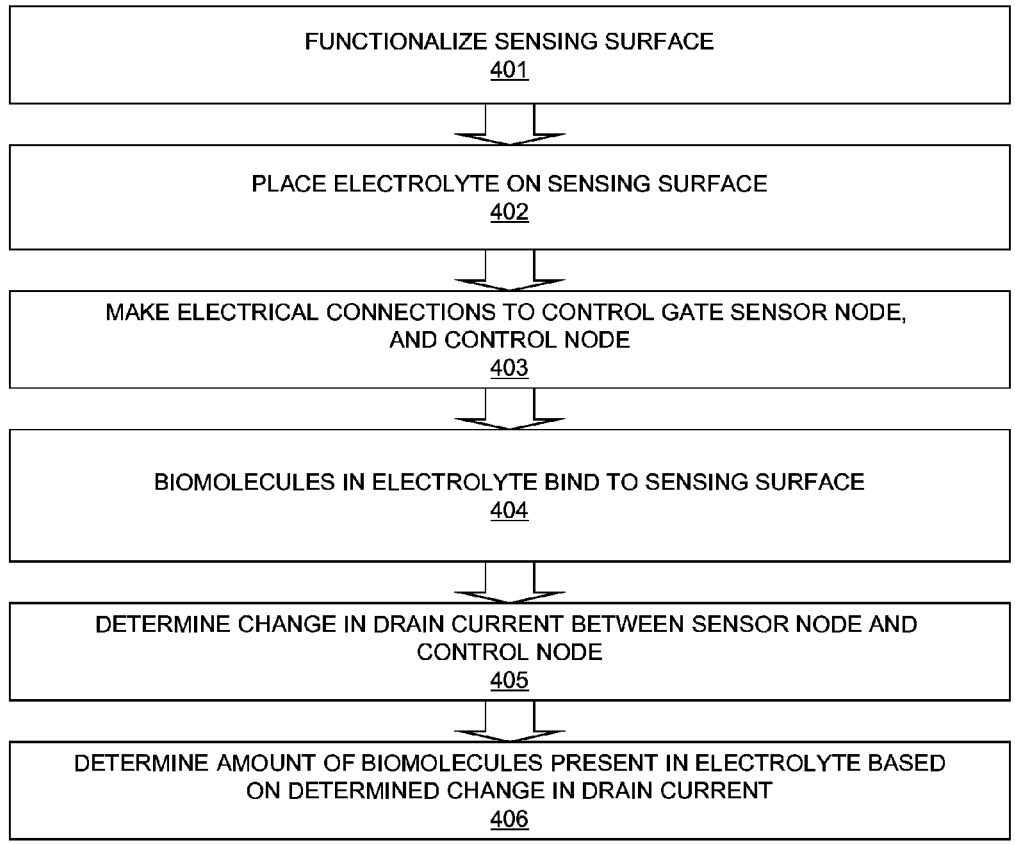
FIG. 4 illustrates an embodiment of a method of operating a dual FET sensor.

FIG. 4 illustrates an embodiment of a method of operating a dual FET sensor 100. FIG. 4 is discussed with respect to FIG. 1; method 400 may also be used in conjunction with the dual sensor FETs 200 and 300 shown in FIGS. 2 and 3. In block 401, gate dielectric surface of the sense FET is functionalized to form the sensing surface 106. Functionalizing of the surface of gate dielectric 105 to form the sensing surface 106 may comprise coating the gate dielectric surface of the sense FET with antibodies or an appropriate chemical that may specifically bind to the particular biomolecules that the sensor is being used to detect in some embodiments. In block 402, electrolyte 108 is placed on sensing surface 106. In block 403, electrical connections are made to control gate 107, sensor node 101, and control node 103. The electrical connections may be made via metal lines connected to each of control gate 107, sensor node 101, and control node 103. A gate voltage is applied to control gate 107 that is sufficient to turn on the control FET. The gate voltage may comprise a constant inversion voltage, and may be between about 11.01 volts (V) and 11.51 V in some embodiments. The control node 103 may be held at a constant voltage $V_d$, which may be about 0.1 V in some embodiments. The sensor node 101 may be held at about 0 V in some embodiments. The shared node 102 and the sense FET gate comprising electrolyte 108 are left floating. In block 404, biomolecules in electrolyte 108 bind to the sensing surface 106. The biomolecules bound to sensing surface 106 causes a change in the workfunction at the interface between the sensing surface 106 and the electrolyte 108, which in turn causes a change in the $I_d$ that flows between the sensor node 101 and the control node 103. In block 405, the change $I_d$ is determined. The change in $I_d$ is determined with respect to a drain current that flows through the sensor 100 in the absence of biomolecules. In block 406, an amount of biomolecules present in electrolyte 108 is determined from the change in $I_d$.

The control FET has a channel length, which is the distance between the control node 103 and the shared node 102. The sense FET also has a channel length, which is the distance between the sensor node 101 and the shared node 102. In some embodiments of dual FET sensor 100, a channel length of the control FET may be shorter than a channel length of the sense FET. Further, the control FET has a channel width, which is the width of the conduction channel of the control FET measured alongside control node 103 in a direction perpendicular to the direction of the drain current flow. The sense FET also has a channel width, which is the width of the conduction channel of the sense FET measured alongside sense node 101 in a direction perpendicular to the direction of the drain current flow. In some embodiments of dual FET sensor 100, a channel width of the control FET may be shorter than a channel width of the sense FET.

The technical effects and benefits of exemplary embodiments include detection of biomolecules or ions in an electrolyte without the need to immerse an electrode in the electrolyte.

The terminology used herein is for the purpose of describing particular embodiments only and is not intended to be limiting of the invention. As used herein, the singular forms "a", "an", and the are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method for operating a sensor for biomolecules or charged ions, the sensor comprising a first field effect transistor (FET) and a second FET, wherein the first FET and the second FET comprise a single shared node, and a sensing surface formed directly on a portion of a gate dielectric comprising SiON, the method comprising:

placing an electrolyte containing the biomolecules or charged ions on the sensing surface of the sensor, the sensing surface located over the single shared node, and the electrolyte comprising a gate of the second FET;

applying an inversion voltage to a gate of the first FET;

making a first electrical connection to an unshared node of the first FET;

making a second electrical connection to an unshared node of the second FET;

leaving the shared node and the gate of the second FET floating;

determining a change in a drain current flowing between the unshared node of the first FET and the unshared node of the second FET, wherein the change in the drain current is caused by the biomolecules or charged ions in the electrolyte binding to the sensing surface of the sense FET; and determining an amount of biomolecules or charged ions contained in the electrolyte based on the determined change in the drain current, wherein the sensor further comprises an insulating material located directly over the gate dielectric, the unshared node of the first FET, the unshared node of the second FET, a gate of the first FET, and the single shared node such that only the gate of the second FET is exposed to the electrolyte during the placing of the electrolyte.

2. The method of claim 1, wherein the sensing surface comprises a coating of antibodies or a chemical configured to bind with the biomolecules or charged ions contained in the electrolyte.

3. The method of claim 1, wherein the sensor for biomolecules or charged ions comprises a substrate, the substrate comprising silicon or silicon-on-insulator.

4. The method of claim 3, wherein the shared node, unshared node of the first FET, and unshared node of the second FET are located in the substrate and each have the same doping type, and the substrate comprises a doping type that is opposite the doping type of the shared node, unshared node of the first FET, and unshared node of the second FET.

5. The method of claim 1, wherein the gate dielectric has an equivalent oxide thickness (EOT) greater than 20 angstroms (Å).

6. The method of claim 1, wherein the gate of the first FET comprises polysilicon or a metal.

* * * * *